US012653706B2

(12) United States Patent
Andersen et al.

(10) Patent No.: US 12,653,706 B2
(45) Date of Patent: Jun. 16, 2026

(54) MEDICAL DEVICE SYSTEM

(71) Applicant: Cook Medical Technologies LLC, Bloomington, IN (US)

(72) Inventors: Simon Voigt Andersen, Naestved (DK); Adria Rodriguez Paz, Frederiksberg (DK); Tina Mørk, Ringsted (DK); Christina Briks Nielsen, Tureby (DK)

(73) Assignee: Cook Medical Technologies LLC, Bloomington, IN (US)

( * ) Notice: Subject to any disclaimer, the term of this patent is extended or adjusted under 35 U.S.C. 154(b) by 536 days.

(21) Appl. No.: 18/218,959

(22) Filed: Jul. 6, 2023

(65) Prior Publication Data

US 2025/0009496 A1      Jan. 9, 2025

(30) Foreign Application Priority Data

Jul. 5, 2023     (GB) ...................................... 2310335

(51) Int. Cl.
A61F 2/95 (2013.01)
A61F 2/07 (2013.01)

(52) U.S. Cl.
CPC .................. A61F 2/95 (2013.01); A61F 2/07 (2013.01); *A61F 2002/9511* (2013.01); *A61F 2220/0075* (2013.01); *A61F 2250/001* (2013.01)

(58) Field of Classification Search
CPC ...... A61F 2/07; A61F 2/95; A61F 2002/9511; A61F 2002/9505; A61F 2002/9534; A61F 2250/001; A61F 2220/0075
See application file for complete search history.

(56) References Cited

U.S. PATENT DOCUMENTS 3,517,128 A     6/1970  Hines
4,585,000 A     4/1986  Hershenson
(Continued)

FOREIGN PATENT DOCUMENTS

AU     2016/256777 B1     4/2017
CN     207562016        7/2018
(Continued)

OTHER PUBLICATIONS

EP extended European Search Report, Application No. 16275124.2, dated Oct. 27, 2016.
(Continued)

*Primary Examiner* — Sarah W Aleman
(74) *Attorney, Agent, or Firm* — MacMillan, Sobanski & Todd, LLC

(57)     ABSTRACT

A medical device system includes a tubular medical device and a diameter reducing arrangement. The tubular medical device comprises a tubular graft body having a proximal end and a distal end. The diameter reducing arrangement is configured for constricting the medical device, and includes a strand section having first and second ends and being immovably secured to the medical device at the first end and at the second end. The second end is a first circumferential distance from the first end by way of a path along the strand section In a constricted configuration of the medical device a first portion of the strand section extends back on itself to form a first double-stranded tail leading to a first loop, the first tail extending circumferentially against the graft body, constricting the medical device by the strand section restricting the first circumferential distance between the first and second ends of the strand section.

22 Claims, 10 Drawing Sheets

(56)                References Cited

U.S. PATENT DOCUMENTS

| | | | |
|---|---|---|---|
| 4,878,906 A | 11/1989 | Lindemann et al. | |
| 4,913,141 A | 4/1990 | Hillstead | |
| 5,443,477 A | 8/1995 | Marin | |
| 5,693,083 A | 12/1997 | Baker et al. | |
| 5,713,907 A | 2/1998 | Hogendijk | |
| 5,843,158 A | 12/1998 | Lenker et al. | |
| 5,971,938 A | 10/1999 | Hart | |
| 6,468,298 B1 | 10/2002 | Pelton | |
| 6,562,064 B1 | 5/2003 | deBeer | |
| 6,692,521 B2 | 2/2004 | Pinchasik | |
| 6,964,677 B2 | 11/2005 | Osypka | |
| 7,160,318 B2 | 1/2007 | Greensberg et al. | |
| 7,306,617 B2 | 12/2007 | Majercak | |
| 7,611,528 B2 | 11/2009 | Goodson, IV et al. | |
| 7,803,177 B2 | 9/2010 | Hartley et al. | |
| 7,909,863 B2 | 3/2011 | Hartley et al. | |
| 8,172,895 B2 | 5/2012 | Anderson et al. | |
| 8,348,988 B2 | 1/2013 | Lad et al. | |
| 8,652,193 B2 | 2/2014 | Dorn | |
| 8,728,148 B2 | 5/2014 | Roeder et al. | |
| 8,926,686 B2 | 1/2015 | King | |
| 8,968,384 B2 | 3/2015 | Pearson et al. | |
| 9,056,008 B2 | 6/2015 | Righini | |
| 9,078,746 B2 | 7/2015 | Pavcnik | |
| 9,198,787 B2 | 12/2015 | Kratzberg et al. | |
| 9,220,617 B2 | 12/2015 | Berra | |
| 9,278,018 B2 | 3/2016 | Roeder | |
| 9,314,355 B2 | 4/2016 | Styrc et al. | |
| 9,427,307 B2 | 8/2016 | Pearson et al. | |
| 9,456,888 B2 | 10/2016 | Chin | |
| 9,498,361 B2 | 11/2016 | Roeder et al. | |
| 9,504,555 B2 | 11/2016 | Hartley et al. | |
| 9,655,712 B2 | 5/2017 | Berra | |
| 9,681,968 B2 | 6/2017 | Goetz | |
| 9,707,072 B2 | 7/2017 | King | |
| 9,713,523 B2 | 7/2017 | Zacharias | |
| 9,757,263 B2 | 9/2017 | Roeder et al. | |
| 9,855,128 B2 | 1/2018 | Kolbel et al. | |
| 9,913,743 B2 | 3/2018 | Arbefeuille | |
| 9,925,032 B2 | 3/2018 | Jensen et al. | |
| 9,925,080 B2 | 3/2018 | Arbefeuille | |
| 9,980,840 B2 | 5/2018 | Havel | |
| 10,172,731 B2 | 1/2019 | Roeder | |
| 10,188,538 B2 | 1/2019 | Eller et al. | |
| 10,350,096 B2 | 7/2019 | Roeder | |
| 10,433,991 B2 | 10/2019 | Baxter et al. | |
| 2001/0041925 A1 | 11/2001 | Konya et al. | |
| 2002/0007208 A1 | 1/2002 | Strecker | |
| 2002/0193872 A1 | 12/2002 | Trout, III et al. | |
| 2003/0050684 A1 | 3/2003 | Abrams et al. | |
| 2003/0050694 A1 | 3/2003 | Yang | |
| 2003/0191516 A1 | 10/2003 | Weldon | |
| 2003/0233140 A1 | 12/2003 | Hartley et al. | |
| 2004/0073289 A1 | 4/2004 | Hartley | |
| 2004/0106978 A1 | 6/2004 | Greenberg et al. | |
| 2004/0138734 A1 | 7/2004 | Chobotov et al. | |
| 2004/0167602 A1 | 8/2004 | Fischell | |
| 2004/0171932 A1 | 9/2004 | Raman et al. | |
| 2004/0193178 A1 | 9/2004 | Nikolchev | |
| 2004/0193244 A1 | 9/2004 | Hartley et al. | |
| 2004/0220655 A1 | 11/2004 | Swanson et al. | |
| 2005/0033406 A1 | 2/2005 | Barnhart | |
| 2005/0085890 A1 | 4/2005 | Rasmussen et al. | |
| 2005/0090887 A1 | 4/2005 | Pryor | |
| 2005/0107862 A1 | 5/2005 | Ohlenschlaeger | |
| 2005/0119722 A1 | 6/2005 | Styrc | |
| 2005/0137701 A1 | 6/2005 | Salahieh et al. | |
| 2005/0288768 A1 | 12/2005 | Sowinski et al. | |
| 2006/0142836 A1* | 6/2006 | Hartley | A61F 2/95 |
| | | | 623/1.11 |
| 2006/0190070 A1 | 8/2006 | Dieck et al. | |
| 2006/0265045 A1 | 11/2006 | Shiu | |
| 2007/0043425 A1 | 2/2007 | Hartley et al. | |
| 2007/0088424 A1 | 4/2007 | Greenberg et al. | |
| 2007/0100427 A1 | 5/2007 | Perouse | |
| 2007/0208409 A1 | 9/2007 | Quigley | |
| 2007/0233223 A1* | 10/2007 | Styrc | A61F 2/95 |
| | | | 606/108 |
| 2007/0250069 A1 | 10/2007 | Carlson | |
| 2008/0027529 A1 | 1/2008 | Hartley et al. | |
| 2008/0077226 A1 | 3/2008 | Ouellette | |
| 2008/0140178 A1 | 6/2008 | Rasmussen et al. | |
| 2008/0243225 A1 | 10/2008 | Satasiya | |
| 2008/0294234 A1 | 11/2008 | Hartley et al. | |
| 2009/0030497 A1 | 1/2009 | Metcalf et al. | |
| 2009/0082842 A1 | 3/2009 | Glynn | |
| 2009/0082847 A1 | 3/2009 | Zacharias | |
| 2009/0099640 A1 | 4/2009 | Weng | |
| 2009/0112302 A1 | 4/2009 | Stafford | |
| 2009/0171431 A1 | 7/2009 | Swanson et al. | |
| 2009/0171437 A1 | 7/2009 | Brocker et al. | |
| 2009/0204202 A1 | 8/2009 | Dierking et al. | |
| 2009/0230169 A1 | 9/2009 | Xiao | |
| 2009/0259291 A1 | 10/2009 | Kolbel et al. | |
| 2010/0010617 A1 | 1/2010 | Goodson, IV et al. | |
| 2010/0168838 A1 | 7/2010 | Hartley et al. | |
| 2010/0211052 A1 | 8/2010 | Brown | |
| 2010/0249896 A1 | 9/2010 | Sugimoto et al. | |
| 2010/0268317 A1 | 10/2010 | Stiger | |
| 2010/0286768 A1 | 11/2010 | Alkhatib | |
| 2010/0324655 A1 | 12/2010 | Styrc | |
| 2011/0054519 A1 | 3/2011 | Neuss | |
| 2011/0087320 A1 | 4/2011 | Bolduc et al. | |
| 2011/0178588 A1 | 7/2011 | Haselby | |
| 2011/0190865 A1 | 8/2011 | McHugo et al. | |
| 2011/0270372 A1 | 11/2011 | Argentine | |
| 2011/0288624 A1 | 11/2011 | Roeder et al. | |
| 2011/0307049 A1 | 12/2011 | Kao | |
| 2012/0010696 A1 | 1/2012 | Greenberg et al. | |
| 2012/0277848 A1 | 11/2012 | Roeder et al. | |
| 2013/0158648 A1 | 6/2013 | Hartley et al. | |
| 2013/0245743 A1 | 9/2013 | Norris | |
| 2014/0135899 A1 | 5/2014 | Chobotov | |
| 2014/0180378 A1 | 6/2014 | Roeder | |
| 2014/0336745 A1 | 11/2014 | Barthold et al. | |
| 2014/0358215 A1 | 12/2014 | Baylis | |
| 2015/0157445 A1 | 6/2015 | Pearson | |
| 2015/0157479 A1 | 6/2015 | Parsons | |
| 2015/0164667 A1 | 6/2015 | Mnluan | |
| 2015/0245934 A1 | 9/2015 | Lombardi | |
| 2015/0313702 A1 | 11/2015 | Mcguckin, Jr. | |
| 2016/0045350 A1 | 2/2016 | Berra | |
| 2016/0113703 A1 | 4/2016 | Danek | |
| 2016/0135972 A1 | 5/2016 | Vad | |
| 2016/0184118 A1 | 6/2016 | Faber et al. | |
| 2016/0199207 A1* | 7/2016 | Treacy | A61F 2/82 |
| | | | 623/1.12 |
| 2016/0213470 A1 | 7/2016 | Ahlberg | |
| 2016/0228681 A1 | 8/2016 | Di Palma | |
| 2016/0235531 A1 | 8/2016 | Ciobanu | |
| 2016/0270910 A1 | 9/2016 | Birmingham | |
| 2016/0278910 A1 | 9/2016 | Kelly | |
| 2016/0310301 A1 | 10/2016 | Moore | |
| 2016/0310303 A1 | 10/2016 | Thapliyal | |
| 2017/0100232 A1 | 4/2017 | Arbefeuille | |
| 2017/0128704 A1 | 5/2017 | Lenihan | |
| 2017/0303927 A1 | 10/2017 | Dickinson | |
| 2018/0028191 A1 | 2/2018 | Bradway | |
| 2018/0036124 A1 | 2/2018 | Tran | |
| 2018/0110610 A1 | 4/2018 | Kölbel | |
| 2018/0110638 A1 | 4/2018 | Berra | |
| 2018/0125634 A1 | 5/2018 | King et al. | |
| 2018/0125688 A1 | 5/2018 | Chambers | |
| 2018/0140418 A1 | 5/2018 | Sandhu | |
| 2018/0200496 A1 | 7/2018 | Kratzberg | |
| 2018/0235788 A1 | 8/2018 | Hyodoh | |
| 2018/0250136 A1 | 9/2018 | Linder-Ganz | |
| 2018/0311030 A1 | 11/2018 | Bradway | |
| 2019/0091051 A1 | 3/2019 | Roeder | |
| 2021/0069468 A1 | 3/2021 | Keating | |
| 2022/0047405 A1 | 2/2022 | Xiao | |
| 2022/0160529 A1 | 5/2022 | Arbefeuille et al. | |
| 2022/0192851 A1 | 6/2022 | Garcia | |
| 2022/0211482 A1* | 7/2022 | Schmidt | A61F 2/07 |

(56) References Cited

U.S. PATENT DOCUMENTS

FOREIGN PATENT DOCUMENTS

| | | |
|---|---|---|
| EP | 0330376 | 8/1989 |
| EP | 0696447 | 2/1996 |
| EP | 0866678 | 9/1998 |
| EP | 0990426 | 4/2000 |
| EP | 2471498 A1 | 7/2012 |
| EP | 2522315 | 11/2012 |
| EP | 2604232 A1 | 6/2013 |
| EP | 2630933 | 8/2013 |
| EP | 2907485 | 8/2015 |
| EP | 3009102 | 4/2016 |
| EP | 3040054 A1 | 7/2016 |
| EP | 3069696 B1 | 9/2016 |
| EP | 3187155 A1 | 7/2017 |
| EP | 3272319 A1 | 1/2018 |
| EP | 3585306 A1 | 8/2018 |
| EP | 3395302 A1 | 10/2018 |
| EP | 3733124 A1 | 11/2020 |
| EP | 4059480 A1 | 9/2022 |
| ES | 2663147 | 4/2018 |
| GB | 2464978 A | 5/2010 |
| GB | 2474252 | 4/2011 |
| GB | 2491478 | 12/2012 |
| JP | H11332892 A | 12/1999 |
| JP | 2000-279532 A | 10/2000 |
| JP | 2001-525218 A | 12/2001 |
| JP | 2004-529735 A | 9/2004 |
| JP | 2006-346350 | 12/2006 |
| WO | 9853761 | 12/1998 |
| WO | 1999051165 | 10/1999 |
| WO | WO 01/74270 A2 | 10/2001 |
| WO | 03068302 | 8/2003 |
| WO | WO 2004/017868 A1 | 3/2004 |
| WO | WO 2004/019823 A1 | 3/2004 |
| WO | 2005002660 | 1/2005 |
| WO | WO 2006/037086 A1 | 4/2006 |
| WO | 2007059018 | 5/2007 |
| WO | 2008066923 | 6/2008 |
| WO | WO 2009/126227 A2 | 10/2009 |
| WO | WO 2010/090699 A1 | 8/2010 |
| WO | 2011049808 | 4/2011 |
| WO | 2011059707 | 5/2011 |
| WO | WO 2011/081997 A1 | 7/2011 |
| WO | 2013118352 | 8/2013 |
| WO | 2013118362 | 8/2013 |

OTHER PUBLICATIONS

EP extended European Search Report, Application No. 16275123.4, dated Oct. 27, 2016.

EP extended European Search Report, Application No. 16275125.9, dated Nov. 28, 2016.

EP extended European Search Report, Application No. 16275126.7, dated Oct. 27, 2016.

EP extended European Search Report, Application No. 16275127.5, dated Oct. 27, 2016.

EP extended European Search Report, Application No. 22275125.7, dated May 17, 2023.

EP extended European Search Report, Application No. 24275032.1, dated Sep. 30, 2024.

EP partial European Search Report, Application No. 16275125.9, dated Oct. 27, 2016.

EP partial European Search Report, Application No. 22275015.0, dated Aug. 29, 2022.

Tilo Kolbel et al., "Staged Proximal Deployment of the Zenith TX2 Thoracic Stent-Graft: A Novel Technique to Improve Conformance to the Aortic Arch," Oct. 1, 2009, https://journals.sagepub.com/doi/abs/10.1583/09-2787.1, vol. 16, 598-602.

Examiner's First Report for AU Application No. 2006279305 dated May 9, 2011, 2 pages.

Examiner's First Report for AU Application No. 2006280948 dated Jul. 25, 2011, 3 pages.

Examiner's First Report for Canadian Application No. 2,619,585 dated Mar. 4, 2013, 3 pages.

Canadian Office Action and Search Report for CA Application No. 2,737,438 dated Aug. 25, 2015, 3 pages.

EP Examination Report for EP Application No. 06801982.7 dated May 9, 2012, 4 pages.

EP Examination Report for EP Application No. 06801982.7 dated Mar. 20, 2015, 3 pages.

EP Examination Report for EP Application No. 06813626.6 dated Jun. 15, 2010, 4 pages.

EP Search Report for EP Application No. 12171060.2 dated Aug. 16, 2012, 4 pages.

EP Examination Report for EP Application No. 12171060.2 dated Dec. 21, 2012, 4 pages.

Extended European Search Report dated Apr. 4, 2013, pp. 1-7, European Patent Application No. 12197088.3, European Patent Office, The Netherlands.

Examination dated Nov. 25, 2016 for European Patent Application No. 12197088.3, 5 pages.

Notice of Opposition of EP Application No. 18710604.2 dated Oct. 28, 2021, 7 pages.

Office Action (English language translation only) for JP Application No. 2008-527206 dated May 31, 2011, 4 pages.

Office Action and English translation for JP Application No. 2008-527220 dated Oct. 18, 2011, 7 pages.

Office Action and English translation for JP Application No. 2008-527220 dated Jun. 26, 2012, 7 pages.

Japanese Office Action and English translation of Japanese Application No. 2011-534517 dated Aug. 21, 2013, 6 pages.

International Preliminary Report and Written Opinion for PCT/US2009/005890 dated Oct. 31, 2008, 11 pages.

Office Action for U.S. Appl. No. 13/970,861, dated Jun. 4, 2015, 11 pages.

Response to Office Action for U.S. Appl. No. 13/970,861, dated Oct. 5, 2015, 9 pages.

Office Action for U.S. Appl. No. 13/713,517, dated Mar. 16, 2015, 20 pages.

Response to Office Action for U.S. Appl. No. 13/713,517, dated Sep. 16, 2015, 9 pages.

Zenith Alpha TM Thoracic Endovascular Graft Instructions for Use brochure, by Cook Medical, I-Alpha-Thoracic-442-03, dated Oct. 2017, 16 pages.

Zenith Dissection Endovascular Graft and Stent Device description by Cook Medical, AI-D19767-EN-PA, saved Dec. 16, 2019, 19 pages.

TEVAR (Thoracic Endovascular Aneurysm Repair) Information for Patients and Families, by Liverpool Heart and Chest Hospital, published Jan. 2013, 32 pages.

Dr. Ali Azizzadeh, "Thoracic Endovascular Aortic Repair," Society for Vascular Surgery, https://vascular.org/patients/vascular-treatments/repair-thoaric-aortic-aneurysm/thoracic-endovascular-aortic-reapir, printed Jan. 4, 2021, 5 pages.

* cited by examiner

MEDICAL DEVICE SYSTEM

RELATED APPLICATIONS

This application priority to UK Application Serial No. 2310335.1 filed on Jul. 5, 2023, the contents of which are hereby incorporated by reference in their entirety.

BACKGROUND

1. Technical Field Text

The present invention relates to a system for reducing the diameter of a medical device, including a tubular graft body, optionally a stent, and a diameter reducing arrangement.

2. Background Information

Aneurysms or ulcers of the thoracic aorta or aortic arch can be treated by insertion of a prosthesis, such as a stent graft, into an appropriate position. Owing to the curvature of the aorta, it is desirable to conform the stent graft, in particular the proximal end of the stent graft, with the curve of the aorta. One known stent graft system for providing proximal end conformance with the curve, as disclosed in US Publication No. 2022/0211482, the contents of which are incorporated by reference herein in their entirety, includes a proximal alignment stent and a sealing stent distal of the alignment stent where a diameter reduction loop first end is attached to the distal end of the sealing stent, the loop extends circumferentially about the stent graft, and the second end of the loop engages a trigger wire. In particular, two opposing loops' first ends may be attached to the stent and the loops extend in opposite directions about the stent graft with the second ends of the loops meeting to engage a release wire.

BRIEF SUMMARY

Disclosed is a medical device system for at least partially constricting a medical device including a tubular medical device, the medical device comprising a tubular graft body having a proximal end and a distal end; a diameter reducing arrangement configured for constricting a diameter of the medical device, the diameter reducing arrangement including a strand section having first and second ends and being secured to the medical device at the first end and at the second end, the second end being a first circumferential distance from the first end by way of a path along the strand section; wherein, in a constricted configuration of the medical device, a first portion of the strand section extends back on itself to form a first double-stranded tail leading to a first loop, the first double-stranded tail extending circumferentially against the graft body to constrict the medical device by the strand section restricting the first circumferential distance between the first and second ends of the strand section.

The first and second ends of the strand section are immovably secured to the medical device, and the first portion of the strand section passes and is laid double circumferentially beyond the first end to form the first tail and first loop. The first circumferential distance traverses and defines a first circumferential region of the medical device, and in an expanded configuration of the medical device, at least a majority of the strand section is disposed in the first circumferential region of the medical device. Further, in an expanded configuration of the medical device at least a majority of the first portion is disposed in the first circumferential region of the medical device. In the constricted configuration, the first circumferential distance traverses and defines a first circumferential region of the medical device, and wherein, in the constricted configuration, the first portion extends outside the first circumferential region. The first loop is retained by a release mechanism, which may be one or more trigger wires to hold the medical device in the constricted configuration.

In the expanded configuration, the first and second ends of the strand section define first and second mutually exclusive circumferential regions of the stent graft with the first circumferential region of the stent graft extending from the first end to the second end of the strand section. Further, in the expanded configuration of the medical device, the first circumferential region extends around at least $\frac{1}{7}$ of the circumference of the medical device, preferably at least $\frac{1}{2}$ and most preferably in the range of $\frac{1}{2}$ to $\frac{5}{6}$ of the circumference of the medical device.

The medical device may be a stent graft including at least one stent attached to the tubular graft body. The stent may be a proximal most body stent, and the strand section may be attached to the tubular graft body at the distal end of the stent. The strand section may engage distal apices of the stent to constrict the distal end of the stent.

Further disclosed is a diameter reduction system for a medical device having a tubular graft body having a proximal end and a distal end; a stent disposed about the tubular graft body adjacent the proximal end of the tubular graft body and at least partially overlapping the tubular graft body; and a diameter reducing arrangement configured for constricting a diameter of the stent, the diameter reducing arrangement including a strand section having first and second ends. The first end is attached to the stent at a first point on the stent and the second end is attached to the stent at a second point circumferentially spaced from the first stent to define a first circumferential distance from the first end by way of a path along the strand section to the second end, In an expanded configuration, the first circumferential distance traverses and defines a first circumferential region of the tubular graft body in which a majority of the strand section is disposed, and in a constricted configuration of the medical device, a first portion of the strand section extends back on itself to form a first double-stranded tail leading to a first loop and a second portion of the strand section extends back on itself to form a second double-stranded tail leading to a second loop. Further, in the constricted configuration, the first double-stranded tail and the second double-stranded tail extend circumferentially about a surface of the graft body in opposite directions to constrict the stent to restrict the first circumferential distance between the first and second ends of the strand section. The first and second loops engage at least one releasable wire, which may be a trigger wire.

In the constricted configuration the strand section entirely encircles the tubular graft and in the expanded configuration only partially encircles the graft. The strand section may be woven in and out of the tubular graft body and the first end may be permanently and immovably knotted to a first apex and the second end may be permanently and immovably knotted to a second apex. In the expanded configuration, the stent has a first distal apex within the first circumferential region, a second distal apex within the first circumferential region, and a third distal apex disposed between the first and second distal apices and outside of the first circumferential region, and wherein the first end is secured to the first distal apex, the second end is secured to the second distal apex.

The strand section may be a diameter reduction strand, such as a length of suture, which has a first terminal end immovably attached to the tubular body at one point on the tubular body and a second terminal end immovably attached to a point on the tubular body circumferentially spaced from the first point to define a length of the diameter reducing strand between the first and second point. In a constricted configuration, a first portion of the diameter reduction strand at the first end extends back on itself to form a first double-stranded tail leading to a first loop, the diameter reduction strand is disposed fully circumferentially about the tubular body, and a releasable wire engages the first loop, and in an expanded configuration, the diameter reducing strand is disposed only partially circumferentially about the body, and upon release of the releasable wire, the first loop is released from its looped configuration. In the constricted configuration a second portion of the diameter reduction strand at the second end extends back on itself to form a first double-stranded tail leading to a second loop engaged with the releasable wire, and upon release of the releasable wire, the second loop is released from its looped configuration.

Also described is a medical device, comprising a tubular medical device comprising a tubular graft body having a proximal end and a distal end; a diameter reducing arrangement configured for constricting a diameter of the medical device, the diameter reducing arrangement including a strand section. In the constricted configuration of the medical device, a first portion of the strand section extends back on itself to form a first double-stranded tail leading to a first loop, the first double-stranded tail extending circumferentially against the graft body to constrict the diameter of the medical device.

BRIEF DESCRIPTION OF THE DRAWINGS

Embodiments of the invention are described below, by way of example only, with reference to the accompanying drawings.

DETAILED DESCRIPTION OF THE DRAWINGS AND THE PRESENTLY PREFERRED EMBODIMENTS

Figure 1A:
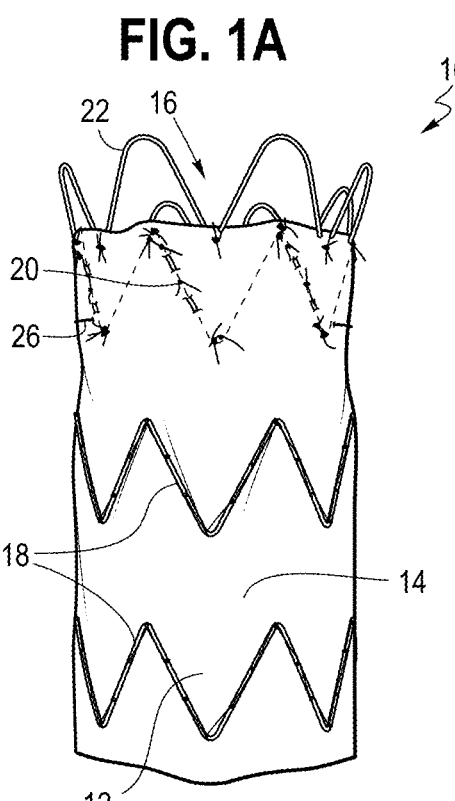
FIGS. 1A-D are a partial views of a stent graft with a diameter reduction arrangement from various sides of the stent graft with the stent graft in an expanded configuration.
Figure 1B:
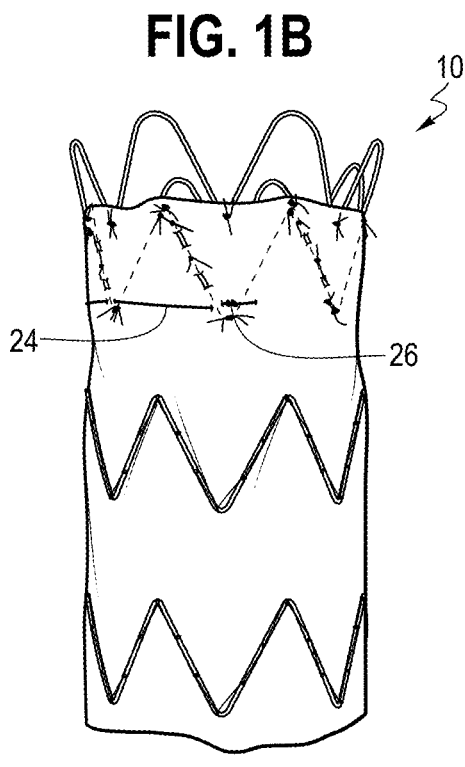
Figure 1C:
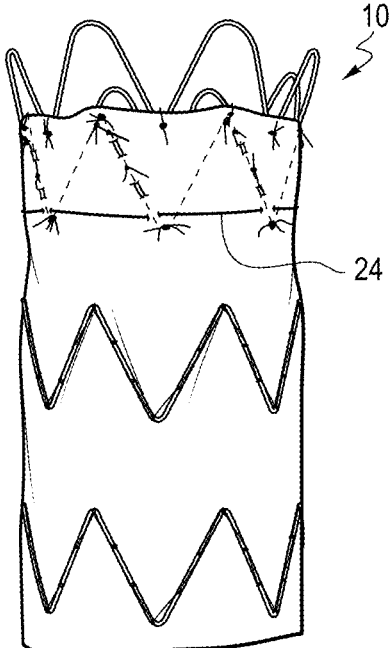
Figure 1D:
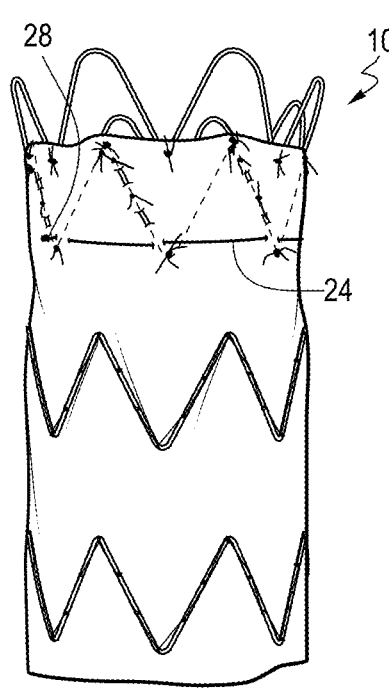

The various embodiments of the invention, as described in detail below, can help prevent the Bird Beak configuration (stent graft malposition) in the curvature of the aortic arch, thus creating an improved chance of procedural success. Also, the diameter reduction arrangement of the invention may be used to constrain a section or all of the stent graft, making it possible to rotate, align and re-align the stent graft.

FIGS. 1A-D show a diameter reduction system for reducing the diameter of a medical device. As shown, the system 10 includes a tubular medical device in the form of a stent graft 12. The stent graft 12 is intended to be implanted in a vessel of the human body, such as the thoracic aorta and/or the aortic arch. FIGS. 1A-D show the stent graft from various sides—of the stent graft with the stent graft in a fully expanded configuration. The stent graft 12 includes a tubular graft body 14 including a proximal open end 16 and a distal open end (not shown), an inner lumen between the proximal and distal ends, and a graft wall.

As shown, the stent graft 12 includes a plurality of body stents 18 attached to and supporting the graft body 14. The body stents 18 each form a ring or hollow cylinder for supporting patency of the lumen of the graft body 14. As shown, the body stents 18 are Z-stents each have a proximal end and a distal end, with struts in a zig-zag pattern around the circumference linking a plurality of proximal apices at the proximal end of the stent to a plurality of distal apices at the distal end of the stent. However, other types of body stents can be used. The body stents can be internal to the stent graft, external to the stent graft or a combination of both. Alternatively, the body stents 18 can be omitted entirely.

The stent graft includes a sealing stent 20 located at and supporting the proximal end 16 of the graft body 14. The sealing stent 20 forms a ring or hollow cylinder for supporting patency of the lumen of the graft body 14 at the proximal end. At least a majority of the sealing stent is overlapped by the graft body 14. As shown, the sealing stent 20 is entirely overlapped by the graft body 14. The sealing stent 20 is a Z-stent having a proximal end and a distal end, with struts in a zig-zag pattern around the circumference linking a plurality of proximal apices at the proximal end of the stent 20 to a plurality of distal apices at the distal end of the stent 20. Nevertheless, in other embodiments other types of stent can be used for the sealing stent. As shown, the sealing stent is an internal stent, however, it can be an external stent in other embodiments. The sealing stent 20 is attached to the graft body 14 by one or more sutures, although in other embodiments other forms of attachment can be used.

The stent graft 12 may also include a bare stent 22 as shown in the figures, however, this is not necessary in every embodiment. The bare stent 22 has a proximal end and a distal end, with struts in a zig-zag pattern linking a plurality of proximal apices at the proximal end of the stent 20 to a plurality of distal apices at the distal end of the stent 20. The distal apices are attached to the graft body 14 at the proximal end 16 of the graft body 14, and the bare stent 22 extends proximally of the graft body 14. As shown, the proximal apices of the bare stent 22 are more rounded and have a greater radius of curvature than the distal apices thereof to reduce pressure exerted on a vessel wall when deployed. Stents having differing radii of curvature of the proximal and distal apices are disclosed in US Publication No. 2009/0171437, the disclosure of which is incorporated by reference herein in its entirety. For example, the radius of curvature of the proximal apices may range from about 3.0 mm to 10.0 mm and the radius of curvature of the distal apices may range from about 0.5 mm to about 1.75 mm. The stents of the stent graft 12 may be self-expanding, balloon expandable, or a combination of self-expanding and balloon expandable stents.

The system 10 includes a diameter reducing arrangement for constricting the stent graft, in particular the sealing stent 20, although the arrangement can be applied to any of the stents. The diameter reducing arrangement includes a strand section 24, for example, as shown here, a length of suture. The strand section 24 has a terminal first end 26 and a terminal second end 28 which, as shown, may be longitudinally level. In other words, the first and second ends 26, 28 are longitudinally level ends of the strand of suture disposed the same longitudinal distance from the proximal edge of the stent graft. The strand section 24 is preferably immovably secured to the stent graft 12 at the first end 26 and at the second end 28, in each case by being tied to the sealing stent 20 with a knot, although the first and second ends can be immovably secured to the stent graft in other fashions. The first and second ends 26, 28 may also be secured to just the graft material, or to both the graft and a stent.

Figures 2, 3:
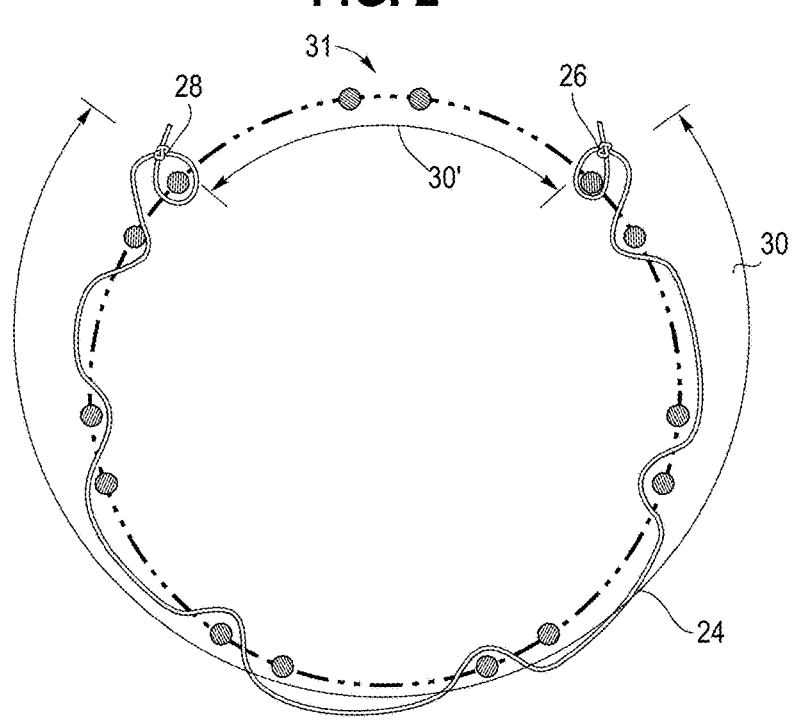
FIG. 2 is a cross-sectional view of the system of the proximal end of the stent graft in the expanded configuration with the diameter reduction arrangement of FIG. 1.
FIG. 3 is a cross-sectional view of the of the proximal end of the stent graft in a constriction configuration with the diameter reduction arrangement of FIG. 1.

As shown in FIG. 2, when the stent graft is in the expanded configuration, the second end 28 is fixed to the stent graft at one point 27 on the stent graft a first circumferential distance away from an attachment point 25 the first end 26 by way of a path along the strand section. In other words, travelling along the strand section 24 from the first end 26 to the second end 28 will result in finishing the first circumferential distance away from the first end 26. The first circumferential distance thereby traverses and defines a first circumferential region 30 of the stent graft where the strand section encompasses the first circumferential region 30 of the stent graft circumferentially between the first 26 and second 28 ends. In this manner, when the stent graft is in the expanded configuration, the first and second ends 26, 28 of the strand section 24 define first 30 and second 30' mutually exclusive circumferential regions of the stent graft between them, the first circumferential region 30 of the stent graft being from the first end 26 to the second end 28 of the strand section, and the second circumferential region 30' being the remainder of the circumference of the stent graft.

In FIG. 2, the strand section 24 is shown to encompass about 4/5 of the circumference of the stent graft in the expanded configuration. That is to say that the first circumferential region 30 extends around 4/5 of the circumference of the stent graft. However, in other embodiments the strand section 24 may encompass different proportions of the circumference (and the first circumferential region may extend around different proportions of the circumference) in the expanded configuration of the stent graft, preferably at least 1/7, more preferably at least 1/2 and most preferably in the range of 1/2 to 5/6 of the circumference.

In the expanded configuration shown in FIG. 1, the strand section extends circumferentially from the first end 26 to the second end 28. As it does so, the angle formed between an arbitrary radius of the stent graft and a radius of the stent graft to a point on the strand section 24, can be considered to increase monotonically as the point travels along the strand section 24 from the first end 26 to the second end 28. In other words, in the expanded configuration, all of the strand section 24 from the first end to the second end is disposed in the first circumferential region 30.

Because the first end and the second end are longitudinally level, the strand section 24 extends in a single plane from the first end 26 to the second end 28 in the expanded configuration. The plane is perpendicular to the longitudinal axis of the stent graft. This minimises the profile of the device and avoids hanging loops. The strand section 24 remains slack in the expanded configuration of the stent graft but is sewn to match the expanded diameter of the graft. In other words, the length of the strand section 24 is slightly greater than (no more than 5% greater than) the circumferential distance from the first end of the strand section 24 to the second end of the strand section 24 when the stent graft is in the expanded configuration. In this way the strand section will not inhibit expansion but will also not have excess suture.

The strand section 24, including the first and second ends 26, 28 thereof, are disposed at and configured to constrict a portion of the sealing stent 20, preferably the distal end of the sealing stent 20. Inn particular the strand section 24 is disposed at and configured to constrict distal apices of the sealing stent 20. The strand section is disposed about the graft and through a majority of the distal apices of the sealing stent 20. For example, the strand section is woven in and out of the graft material and through a majority of the distal apices.

FIG. 2 shows a cross-section through the stent graft system 10 of FIG. 1 in the region of the strand section 24 and looking distally. As shown in FIGS. 1 and 2, from the first end 26 to the second end 28, the strand section 24 passes generally around the outside of the graft body 14 except that it passes around the inside of the second strut of each distal apex of the sealing stent 20 that it passes (with the exception of the apex where the second end 28 is attached), penetrating to the interior of the graft body 14 on one side of the strut and returning to the outside of the graft body 14 on the other side of the strut, before passing to the adjacent apex on the outside of the graft body 14. For the apex where the second end 28 is attached, the strand section passes around the inside of the first strut in the manner described above, and is then knotted to the second strut.

As shown in FIGS. 1-2, in the expanded configuration of the stent graft the first 26 and second 28 ends are circumferentially spaced and the strand section has a length from the first end 26 to the second end 28 which is less than the circumference of the stent graft 12 in the expanded configuration, although this is not necessary in every embodiment. As a result, some apices and interstices are free from the strand section in the expanded configuration of the stent graft. The stent graft of FIG. 1 has a diameter in the expanded configuration of 40-42 mm and the sealing stent 20 has seven distal apices and seven proximal apices, although any expanded configuration can be used and the number of apices does not need to be the same in every embodiment, as described in more detail below.

As shown, six distal apices of the sealing stent 20 and their five intermediate distal interstices are sewn (herein sewn apices/interstices are those that in the expanded configuration of the stent graft are located in the first circumferential region 30 and have the strand section 24 pass them and, in the case of apices, preferably have the strand section sewn over a strut thereof, as shown FIG. 2). Also as shown in FIG. 2, one distal apex 31, together with the two adjacent distal interstices 23, 25, (as well as two proximal apices) of the sealing stent 20 are free (herein free apices/interstices are those that in the expanded configuration of the stent graft are located outside the first circumferential region 30—in other words are in the second circumferential region—and are free from the strand section, that is are not passed by the strand section). This gives a ratio between the circumferential extent of the first circumferential region and the circumferential extent of the second circumferential region of about 5:2. As shown in FIG. 2, the first and second ends 26, 28 of the strand section are knotted to distal apices adjacent to and either side of the free distal apex 31, in particular to the struts thereof that are adjacent to the free distal apex 31.

A constricted configuration of the stent-graft is shown in FIG. 3. In the constricted configuration, a first portion 32 of the strand section extends back on itself to form a first double-stranded tail 34 leading to a first loop 36. In particular, from the first circumferential region 30 the first portion 32 passes the first end 26 and extends outside the first circumferential region 30 into the second circumferential region, where it is laid double circumferentially beyond the first end 26 to form the first tail 34 and first loop 36. As shown, the first tail 34 extends double-stranded circumferentially against the graft body, that is against a surface of the graft body, in this embodiment around part of the exterior of the graft body 14, constricting the stent by the strand section restricting the first circumferential distance between the first and second ends 26, 28 of the strand section 24. In particular, the first portion 32 extending into the second circumferential region and being laid double reduces the length of strand section 24 that is disposed in the first circumferential region 30, thereby forcibly constricting the first circumferential region 30.

Similarly, as shown in FIG. 3, a second portion 38 of the strand section 24 extends back on itself to form a second double-stranded tail 40 leading to a second loop 42. In particular, from the first circumferential region 30 the second portion 38 passes the second end 28 and extends outside the first circumferential region 30 into the second circumferential region, where it is laid double circumferentially beyond the second end 28 to form the second tail 40 and second loop 42. Similarly to the first tail 34, the second tail 40 extends double-stranded circumferentially against the graft body 14, that is against a surface of the graft body, in this embodiment around part of the exterior of the graft body 14, constricting the stent by the strand section 24 restricting the first circumferential distance between the first and second ends 26, 28 of the strand section. In particular, the second portion 38 extending into the second circumferential region and being laid double reduces the length of strand section 24 that is disposed in the first circumferential region 30, thereby forcibly constricting the first circumferential region 30. As shown, a majority of each of the first and second tails 34, 40 is against an exterior surface of the graft body 14. As it further can be seen, the first and second tails 34, 40 extend against the graft body 14 in opposite circumferential senses, meaning that a circumferential direction along the first tail 34 towards the first loop 36 is in an opposite circumferential sense from a circumferential direction along the second tail 40 towards the second loop 42.

As shown in FIG. 3, the first and second tails 34, 40 pass through the wall of the graft body 14 into the interior of the graft body such that the first and second loops 36, 42 are internal to the graft body. As shown The first and second tails 34, 40 pass through the wall of the graft body 14 between the struts of the free distal apex 31, which can be referred to as the holding apex 31, as it is where the tails pass through the wall to be retained. The holding apex 31 is in this embodiment configured to be on the outside of the curve when the stent graft is placed in a curved body vessel. As shown In the constricted configuration of the stent graft, every distal apex of the sealing stent 20 is overlapped by the strand section, whether on the inside or the outside. However, while preferable, this is not essential in every embodiment.

Figure 4:
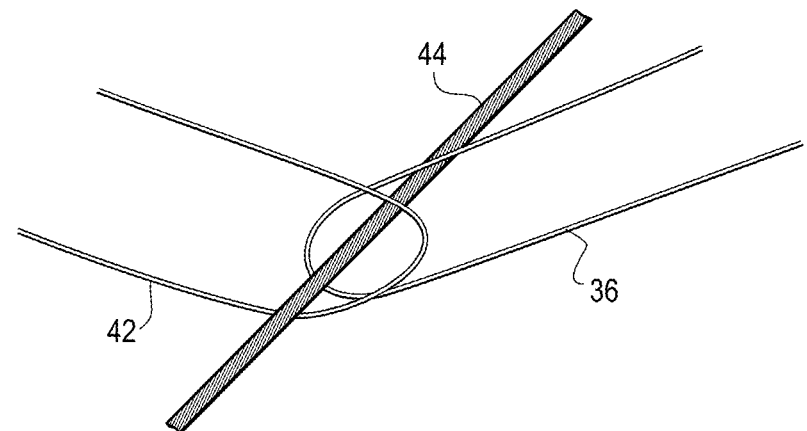
FIG. 4 shows the coupling of a trigger wire with the diameter reduction arrangement of FIG. 1.

For the purposes of deployment, an introducer assembly includes a release mechanism including a trigger or release wire 44, which passes through the lumen of the graft body 14. In the constricted configuration of the stent graft, the first and second loops 36, 42 are retained and locked by the trigger wire 44 internally to the graft body 14 to hold the stent graft in the constricted configuration. However, the first and second loops 36, 42, may be retained and locked by the trigger wire 44 externally to the graft body 14 to hold the stent graft in the constricted configuration. Further, the first and second loops 36, 42 are retained and locked by the trigger wire 44 both internally and externally to the graft body 14 to hold the stent graft in the constricted configuration, for example where the trigger wire extends in and out of the graft material of the graft body along its length. As shown in FIG. 4, the trigger wire 44 passes through both loops 36, 42. However, in other embodiments, one loop (loop A) can pass through the other loop (loop B), and the trigger wire can pass through loop A, as shown in FIG. 5.

Figure 5:
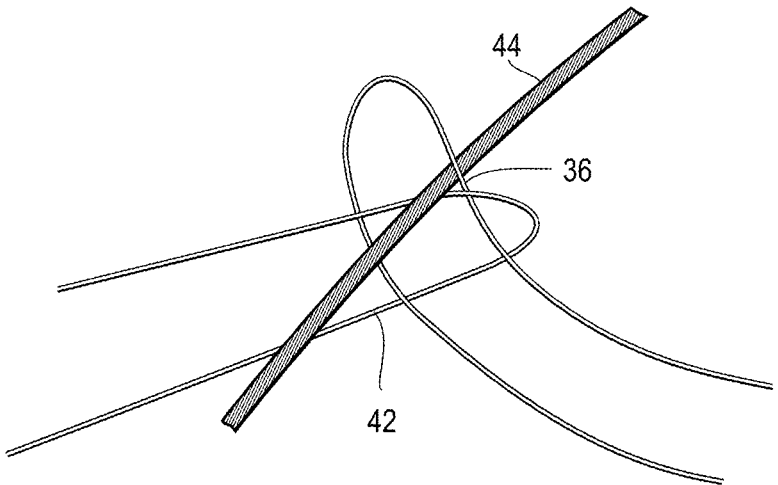
FIG. 5 is a view of another example of the coupling of a trigger wire with the diameter reduction arrangement.
Figure 6:
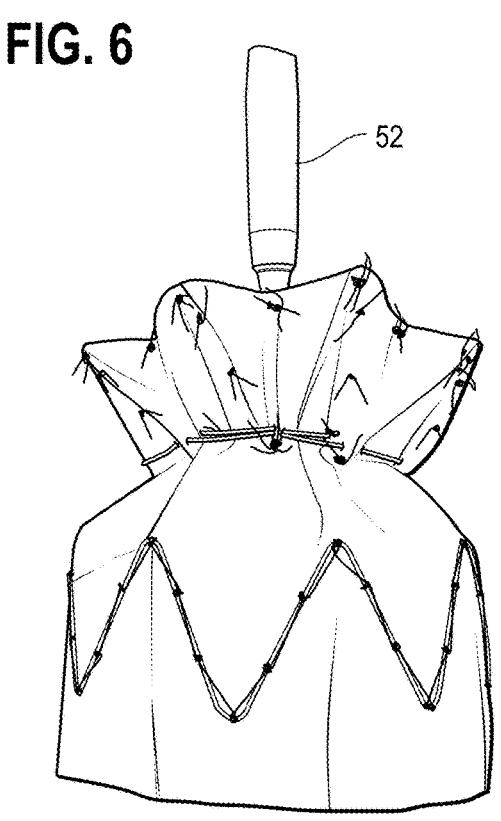
FIG. 6 is a view of an diameter reduction arrangement of FIG. 1, with the stent graft in the constricted configuration and mounted on a delivery device.
Figure 7:
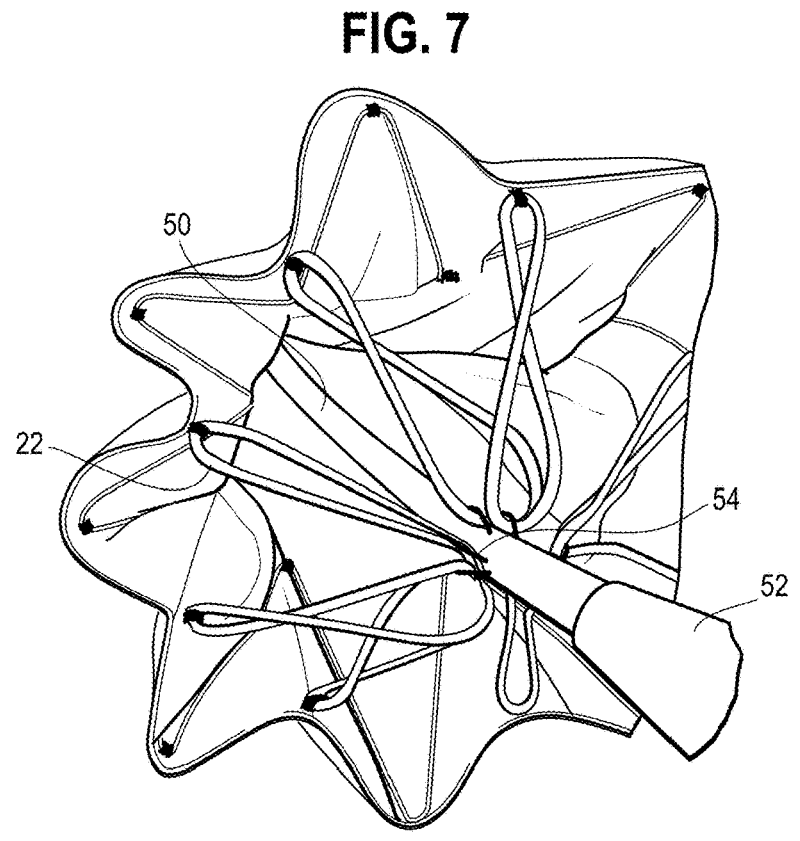
FIG. 7 is an end view of the diameter reduction arrangement of FIG. 6.
Figure 9:
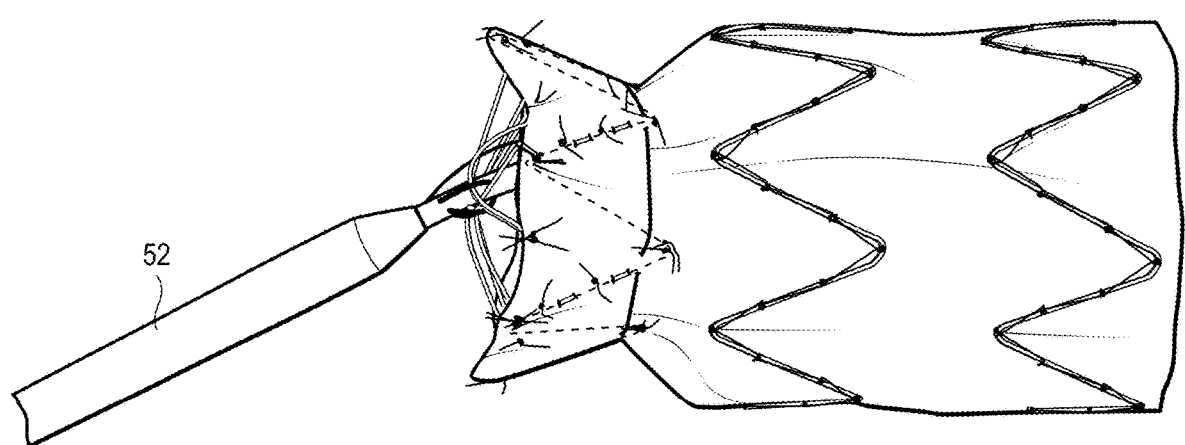
FIG. 9 is a side view of the diameter reduction arrangement of FIG. 6.
Figure 10A:
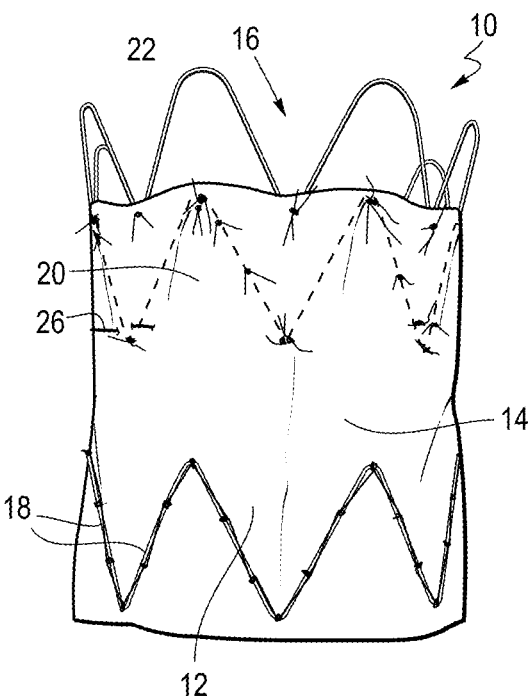
FIG. 10A-D show a stent graft with a diameter reduction arrangement according to another embodiment of the invention.
Figure 10B:
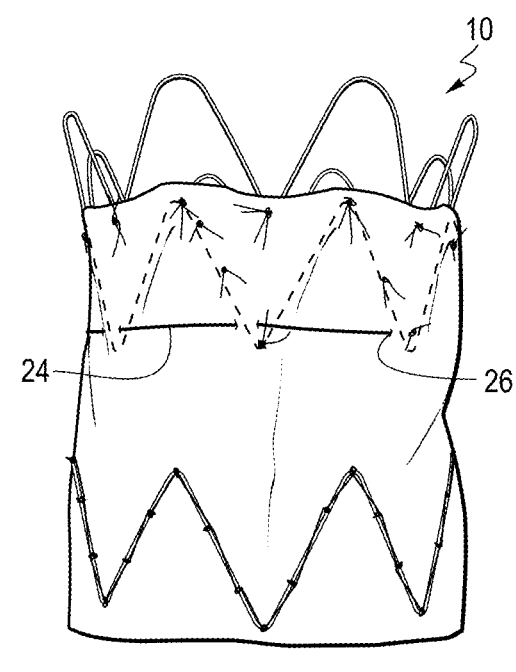
Figure 10C:
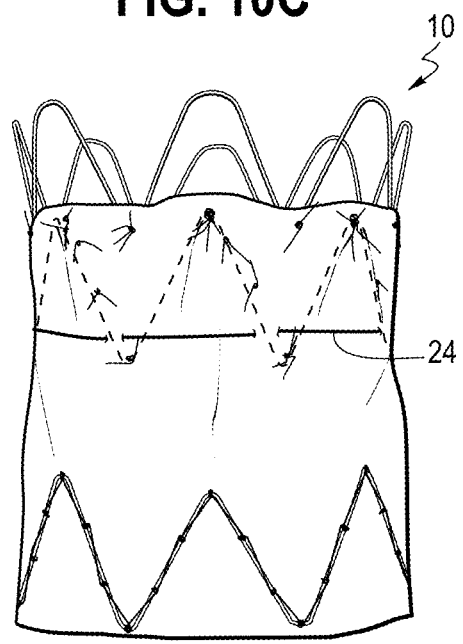
Figure 10D:
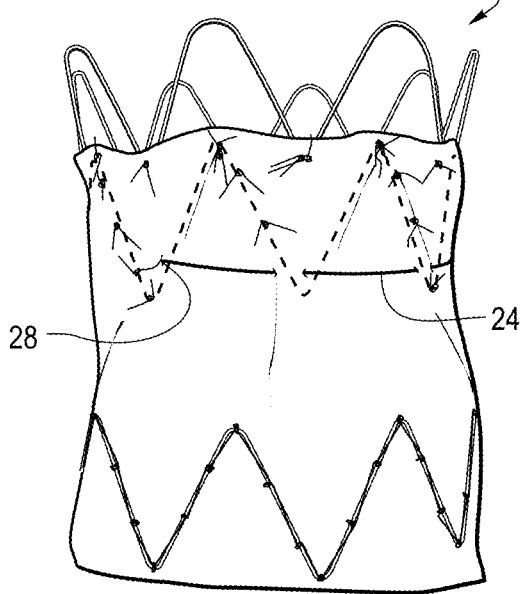

In FIG. 5, loop A is the first loop 36 and loop B is the second loop 42, but they could be the other way around in other embodiments. FIGS. 6 to 7 and 9 show an arrangement including the system of FIG. 1 in the delivery state and the introducer assembly, the introducer assembly including a delivery device onto which the stent graft is mounted in the constricted configuration. The delivery device includes a urethane tubing (UAT) 50 and a nose cone 52 coupled to the UAT 50 at the end which would be furthest from the clinician during a procedure. The UAT 50 extends through the lumen of the graft body 14 and the stent graft 12 is constricted about the UAT 50.

As shown in in FIG. 7 for example, the bare stent 22 is held to the UAT at its proximal apices in a conventional manner using bare stent trigger wires 54 which extend through the UAT, and out of the UAT to loop around one or more proximal apices of the UAT, and return into the UAT to extend within the UAT to be secured within the UAT or within the nose cone 52. Here, the trigger wire 44 is separate from the bare stent trigger wires 54, but in other embodiments the trigger wire 44 can also serve as a bare stent trigger wire. As shown, the trigger wire 44 is attached to the UAT on the inside of the graft. The trigger wire 44 extends from a manipulation section (not shown) through the UAT, and extends out of the UAT in the region of the stent graft to pass through the loops 36, 42 as discussed above, and return into the UAT to extend within the UAT to be secured within the UAT or within the nose cone 52.

Figure 8:
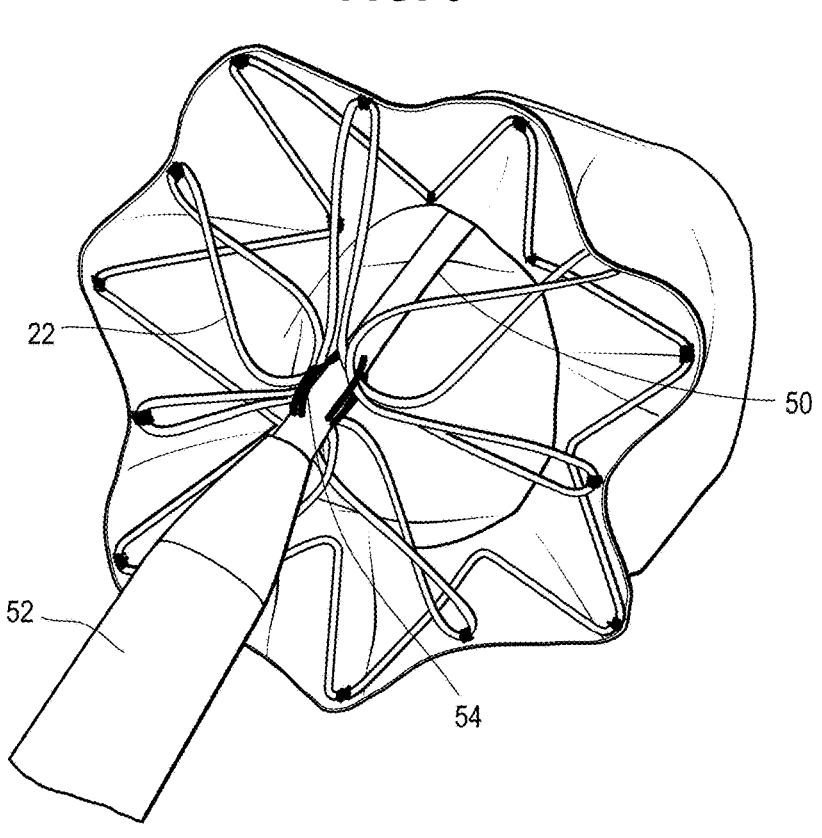
FIG. 8 is an end view of another diameter reduction arrangement with the stent graft in the constricted configuration and mounted on a delivery device.

However, in other embodiments, the trigger wire 44 can be fixed to the side of the UAT rather than extending within it, or can be 'floating', in that it is not held against or in the UAT but is independent of the UAT and secured at the nose cone 52, as shown in FIG. 8, which is otherwise the same as the arrangement of FIG. 7. With a 'floating' trigger wire, the trigger wire can optionally retain the first and second loops 36, 42 on the outside of the graft body 14, in which case the first and second tails 34, 40 do not need to pass through the wall of the graft body. As shown, the trigger wire 44 retains the loops 36, 42 such that they will be on the outside of the curve when introduced into the aorta.

In a method of making the stent graft system, a stent graft is provided in the expanded configuration and the strand section is applied to the stent graft using a needle or other appropriate tool in order to form the system shown in FIG. 1. The materials and tools for making the stent graft system and constricting the stent graft can be standard materials and tools for fabrication of stent grafts. In the method, with the stent graft in the expanded configuration as shown for example in FIG. 1, all of the strand section is disposed in the first circumferential region 30. The method includes pulling the first portion 32 of the strand section 24 to form the first loop 36 and the first double-stranded tail 34 leading to the first loop 36. The method includes using a conventional stylet or pert (although other tools can be used in other embodiments) to lift the strand section 24 adjacent to the first end 26 away from the surface of the graft body 14, thereby forming a bight which forms the first portion 32 and the first loop 36. The first loop 36 then is pulled by the stylet or pert, thereby pulling more of the strand section 24 into the first portion 32, thereby constricting the stent graft and producing the first tail 34.

The method includes pulling the first loop 36 past and circumferentially beyond the first end 26, outside the first circumferential region 30 into the second circumferential region, and extending the first tail 34 circumferentially against the graft body in the second circumferential region, in this embodiment around part of the exterior of the graft body 14. As discussed, this constricts the stent by restricting the first circumferential distance between the first and second ends of the strand section 24. The method also includes pulling the second portion 38 of the strand section 24 to form the second loop 42 and the second double-stranded tail 40 leading to the second loop 42.

The method includes using the stylet or pert to lift the strand section 24 adjacent to the second end 28 away from the surface of the graft body 14, thereby forming a bight which forms the second portion 38 and the second loop 42. The second loop 42 then is pulled by the stylet or pert, thereby pulling more of the strand section 24 into the second portion 38, thereby constricting the stent graft and producing the second tail 40. Similarly to the first loop 36, the method includes pulling the second loop 42 past and circumferentially beyond the second end 28, outside the first circumferential region 30 into the second circumferential region, and extending the second tail 40 circumferentially against the graft body in the second circumferential region, in this embodiment around part of the exterior of the graft body 14. As discussed, this constricts the stent by restricting the first circumferential distance between the first and second ends of the strand section 24. The method includes extending the first tail 34 and second tail 40 through the wall of the graft body into the interior of the graft body and looping the first loop 36 and the second loop 42 around the trigger wire 44 at the interior of the graft body as discussed above.

In use, the stent graft system is introduced into a vessel, in this embodiment into the aorta, endoluminally in a conventional manner with the stent graft in the constricted configuration. Once the stent graft is at the desired deployment site, the stent graft can be partially deployed, for example by retraction of a sheath (not shown). The stent graft can then be fully deployed and implanted in the vessel by retraction of the trigger wire 44.

Once the trigger wire is retracted from the loops 36, 44, the sealing stent 20 is free to expand, allowing the stent graft 12 to expand to the expanded configuration and come into apposition with the vessel walls. This will happen automatically because the stents are self-expanding stents, but in other embodiments the sealing stent 20 and/or other stents may be expanded for example using a balloon.

As the sealing stent 20 expands, the first and second tails 34, 40 are pulled out from the interior of the graft body 14, and the first and second portions 32, 38 are pulled back into the first circumferential region 30. This retraction maintains a low profile for the device during expansion, while retrieving the loops 36, 42 from the interior of the stent graft, thereby minimising any potential undesired interaction of the strand section and loops with other components.

Figure 11:
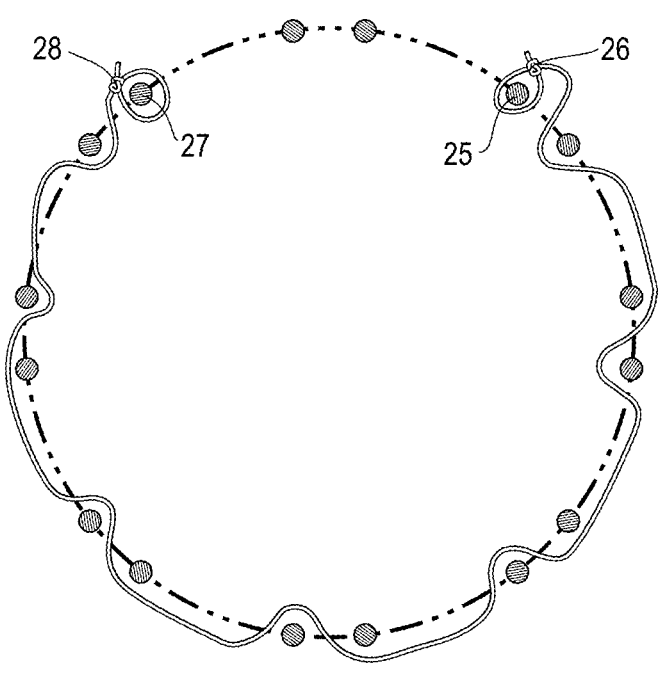
FIG. 11 shows a cross-section of the proximal end of the stent graft of FIG. 10 in an expanded configuration.

FIGS. 10*a* to 10*d* show a system according to another embodiment of the invention with the stent graft in the expanded configuration. The embodiment of FIGS. 10*a* to 10*d* is the same as the embodiment of FIG. 1, including details of manufacture and use, except that the stent graft has a diameter in the expanded configuration of 44 to 46 mm, and the sealing stent has 8 distal apices and 8 proximal apices. As with the system of the embodiment of FIG. 1, there is only one free distal apex (with its two adjacent distal interstices also free) in the expanded configuration of the stent graft, which means that in this embodiment there are seven sewn distal apices with six sewn intermediate distal interstices, and a ratio of the circumferential extent of the second circumferential region to the circumferential extent of the first circumferential region of 1:3. FIG. 11 shows a cross-section of the system of FIG. 10 in the expanded configuration, FIG. 11 being a cross-section through the stent graft system of FIG. 10 in the region of the strand section and looking distally.

Figure 12:
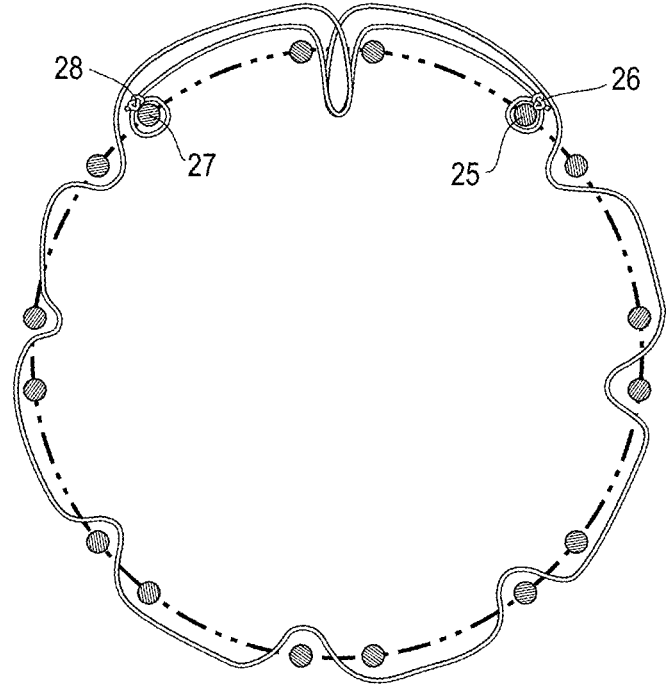
FIG. 12 shows a cross-section of the proximal end of the stent graft of FIG. 10 in a constricted configuration.

FIG. 12 shows a cross-section of the system of FIG. 10 from the same perspective as FIG. 11, but with the stent graft in the constricted configuration. As shown, the constricted configuration is formed and configured in a similar manner to the embodiment of FIG. 1.

Figure 13:
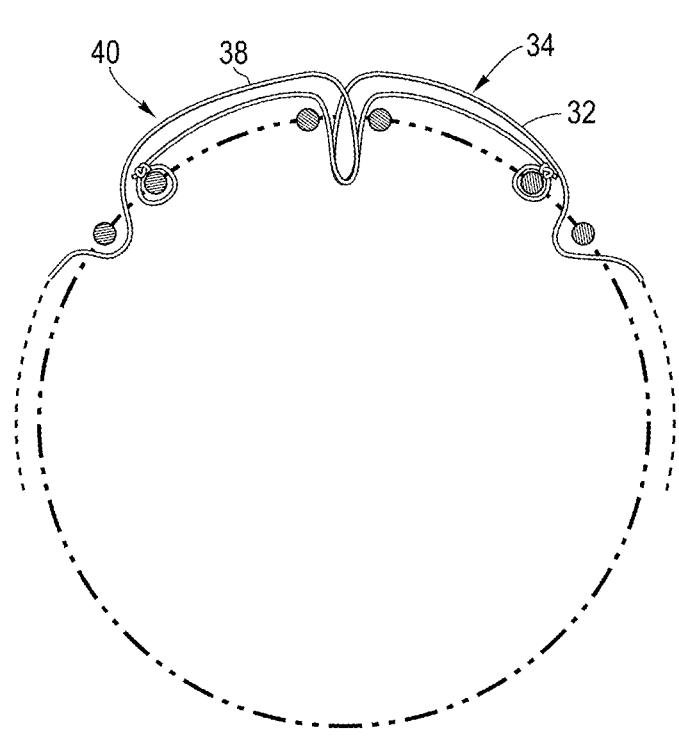
FIGS. 13-18 show cross-sectional views of the proximal end of a stent graft with various diameter reduction arrangements according to the invention.

FIG. 13 is a cross-sectional view of a system as per the embodiment of FIG. 1, the cross-section being through the stent graft system in the region of the strand section with the stent graft in the constricted configuration and looking distally. As represented by FIG. 13 (and FIGS. 14 to 18), the number of sewn distal apices/interstices of the sealing stent can be varied. In addition, the number of free distal apices/interstices of the sealing stent can also be varied. For example, there can be more than or less than one free distal apex and two free distal interstices of the sealing stent. In an expanded configuration of the stent graft a ratio of the number of distal apices of the sealing stent in the second circumferential region (that is free distal apices) to the number of distal apices in the first circumferential region (that is sewn distal apices) may depend on the application. However, preferably this ratio is in the range of 1:2 to 1:7 as this is likely to cover most applications. A preferred ratio between the circumferential extents of the second and first circumferential regions in the expanded configuration of the stent graft is from 1:2 to 1:5. A preferred ratio between the number of distal interstices of the sealing stent in the second circumferential region to the number of distal interstices of the sealing stent in the first circumferential region in the expanded configuration of the stent graft is from 1:2 to 1:5. This ratio can be achieved with any of the configurations depicted in the accompanying figures.

Examples of the number of free distal interstices (in the second circumferential region) to sewn distal interstices (in the first circumferential region) in the expanded configuration of the stent graft for sealing stents with different total numbers of distal apices are given in the following table.

| Stent total number of distal apices | Free distal interstices (in the second circumferential region) | Sewn distal interstices between distal apices (in the first circumferential region) | Ratio |
|---|---|---|---|
| 5 | 1 | 4 | 1/4 |
| 6 | 1 | 5 | 1/5 |
| 7 | 2 | 5 | 2/5 |
| 8 | 2 | 6 | 1/3 |
| 9 | 2 | 7 | 2/7 |
| 10 | 3 | 7 | 3/7 |
| 11 | 3 | 8 | 3/8 |
| 12 | 3 | 9 | 1/3 |
| 13 | 3 | 10 | 3/10 |
| 14 | 4 | 10 | 2/5 |

As shown, in the embodiment of FIG. 13, together the first and second tails 34, 40 span two distal interstices in the constricted configuration of the stent graft. Preferably the first and second tails 34, 40 are arranged symmetrically in the constricted configuration of the stent graft in that they extend against the graft body 14 for the same distance and overlap the same number of apices of the sealing stent 20, as in the systems described above. However, in other embodiments they can be arranged in an asymmetric manner. For example, they can extend against the graft body 14 for different lengths, and/or the free distal apex of the sealing stent 20 can be fully or partially spanned by one of the tails and not the other tail, and/or if there is more than one free distal apex of the sealing stent 20, one tail can span more of the free distal apices than the other tail. One tail can span more free distal interstices of the sealing stent 20 than the other.

Furthermore, although in the above embodiments there are first and second portions 32, 38 forming first and second tails 34, 40, it is possible in some embodiments to just use one portion forming one tail and loop. It is also possible in other embodiments to use multiple strand sections around different parts of the circumference of the stent graft, each configured as described herein, and thereby have any number of tails and loops, however preferably such that every distal apex of the sealing stent is overlapped by a strand section in the constricted configuration of the stent graft.

Figure 14:
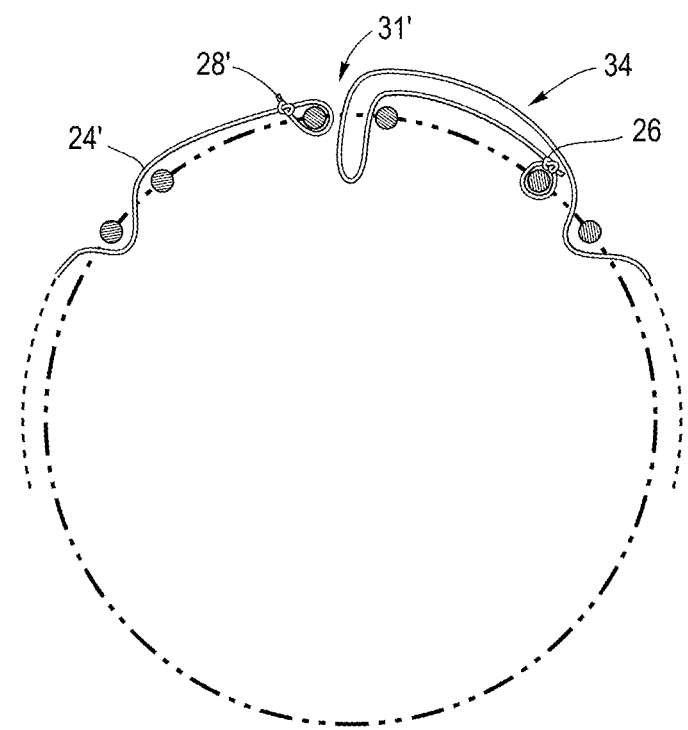

One example of a system which uses one tail and one loop is shown in FIG. 14. FIG. 14 is a cross-section through the stent graft system in the region of the strand section 24' and looking distally, with the stent graft in the constricted configuration. The embodiment of FIG. 14 is the same as the embodiment of FIG. 1 or FIG. 10, including details of manufacture and use, with the following changes. As shown, the second portion, second tail, and second loop are not present in this example. The first portion 32, first tail 34 and first loop 36 are the same as in the system of FIG. 1, but there is no completely free apex in this example.

As shown in FIG. 14, the holding apex 31' is partially free (in other words it is partially in the first circumferential region and partially in the second circumferential region). Only one of the distal interstices of the sealing stent is free, adjacent to the holding apex 31'. In particular, the second end 28' of the strand section 24' is located at one strut of the holding apex 31' with the other strut being free. As shown in FIG. 14, in the constricted configuration the first tail 34 passes the free distal interstice over the free strut of the holding apex 31' and through the wall of the graft body 14 between the struts of the holding apex 31' where it is retained by the trigger wire 44 (not shown in FIG. 14) internally to the graft body 14. Therefore, in the constricted configuration of the stent graft, the first tail spans a single distal interstice.

Figure 15:
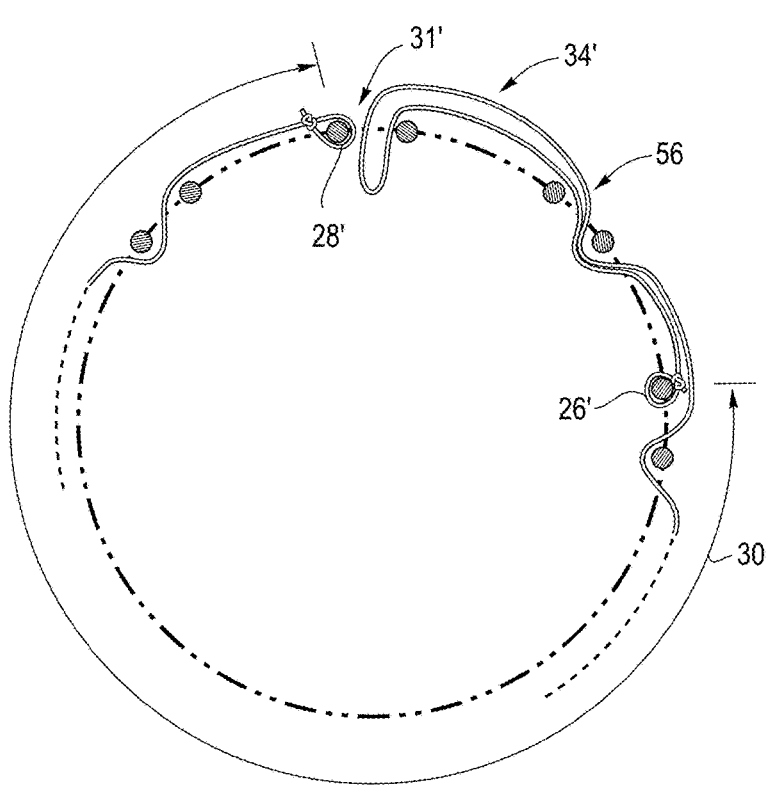

FIG. 15 is a view of a system according to an embodiment which is the same as the embodiment of FIG. 14, including details of manufacture and use, except as discussed below. FIG. 15 is a cross-section through the stent graft system in the region of the strand section and looking distally, with the stent graft in the constricted configuration. In the system of FIG. 15, in addition to the holding apex 31' which is partially free, there is also a completely free second distal apex 56 between the first end 26 of the strand section and the holding apex 31'. There are therefore two free distal interstices of the sealing stent, both to the same side of the holding apex 31', with one on each side of the second apex 56. As discussed earlier, what is meant by a free distal apex/interstice is a distal apex/interstice of the sealing stent that is in the second circumferential region, and is therefore not spanned by the strand section 24 in the expanded configuration of the stent graft 12.

As shown in FIG. 15, in the constricted configuration of the stent graft 12, the first tail 34' is sewn through the second apex 56. In other words, a majority of the first tail 34' extends around the outside of the graft body 14 from the first end 26 of the strand section 24 to the holding apex 31'; however it passes around the inside of the first strut of the second apex 56, penetrating to the interior of the graft body 14 on one side of the strut and returning to the outside of the graft body 14 on the other side of the strut, before passing to the holding apex 31' on the outside of the graft body 14. In other words, the first tail 34' spans one and a half distal apices and two distal interstices in the constricted configuration of the stent graft.

Figure 16:
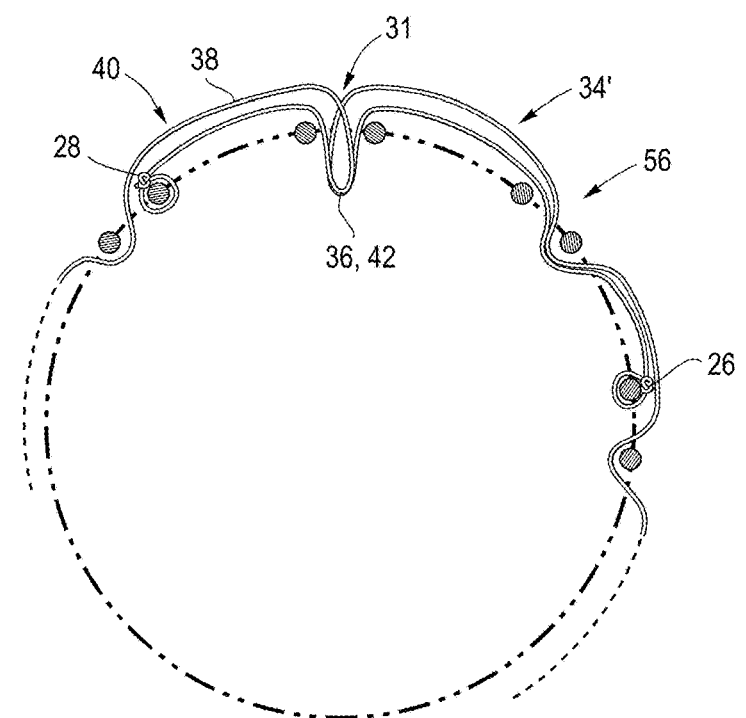

FIG. 16 is a view of a system according to an embodiment which is the same as the embodiment of FIG. 15, including details of manufacture and use, except as discussed below. FIG. 16 is a cross-section through the stent graft system in the region of the strand section and looking distally, with the stent graft in the constricted configuration. Further to the system of FIG. 15, the system of FIG. 16 additionally includes the second portion 38, second tail 40, and second loop 42 of the system of FIG. 1 and, as per FIG. 1, the second end 28 of the strand section is located at a distal apex adjacent to the holding apex 31 but on the opposite side from the second apex 56. The first and second loops 36, 42 are retained by the trigger wire (not shown in FIG. 16) as discussed in respect of the system of FIG. 1. In this embodiment, therefore, three distal interstices of the sealing stent are together spanned by the first and second tails in the constricted configuration of the stent graft.

Figure 17:
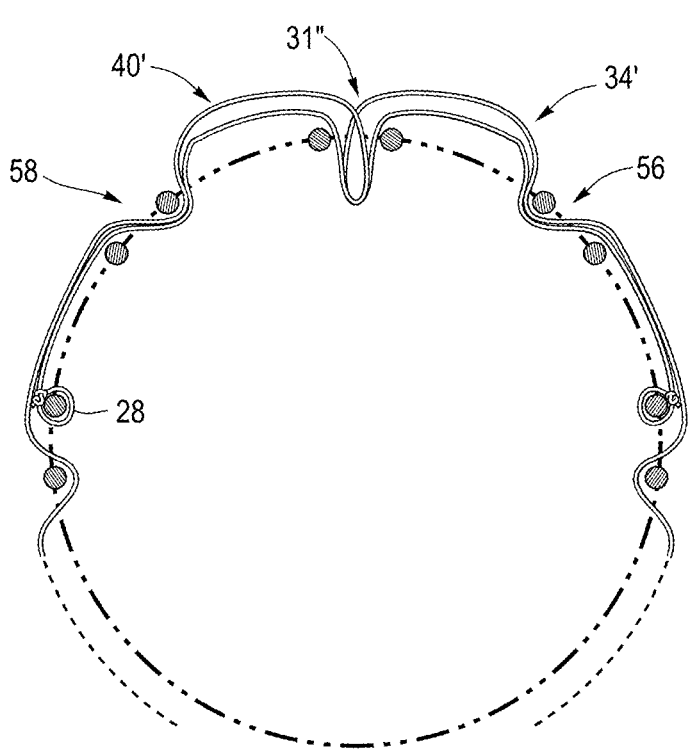

FIG. 17 is a view of a system according to an embodiment which is the same as the embodiment of FIG. 16, including details of manufacture and use, except as discussed below. FIG. 17 is a cross-section through the stent graft system in the region of the strand section and looking distally, with the stent graft in the constricted configuration. In the system of FIG. 17, in addition to the holding apex 31" and the second apex 56, which are completely free, there is also a completely free third distal apex 58 located on the opposite side of the holding apex 31" from the second apex 56 and located between the second end 28 of the strand section and the holding apex 31". There are therefore four free distal interstices of the sealing stent, two on each side of the holding apex 31', which are laid out with one on each side of the second apex 56, and one on each side of the third apex 58. As discussed earlier, what is meant by a free distal apex/interstice is a distal apex/interstice of the sealing stent that is in the second circumferential region, and is therefore not spanned by the strand section 24 in the expanded configuration of the stent graft 12.

As shown in FIG. 17, in the constricted configuration of the stent graft 12, the second tail 40' is sewn through the third apex 58. In other words, a majority of the second tail 40' extends around the outside of the graft body 14 from the second end 28 of the strand section 24 to the holding apex 31"; however it passes around the inside of the second strut of the third apex 58, penetrating to the interior of the graft body 14 on one side of the strut and returning to the outside of the graft body 14 on the other side of the strut, before passing to the holding apex 31' on the outside of the graft body 14. In other words, the second tail 40' spans one and a half distal apices and two distal interstices in the constricted configuration of the stent graft, meaning that together the first and second tails span four distal interstices in the constricted configuration of the stent graft.

As shown in FIG. 17, in this system the first tail passes around the inside of the second strut of the second apex 56 rather than the inside of the first strut of the second apex 56 as in FIG. 16 (the numbering of the strut representing the circumferential order away from the end of the strand section 24 from which the respective tail extends). However, where the strand section 24 and/or tails 24, 40 pass around the inside of one strut of an apex, either strut can be selected. In addition to the above, it is possible in some embodiments for the tails to pass through the wall of the graft body at different locations from each other.

Figure 18:
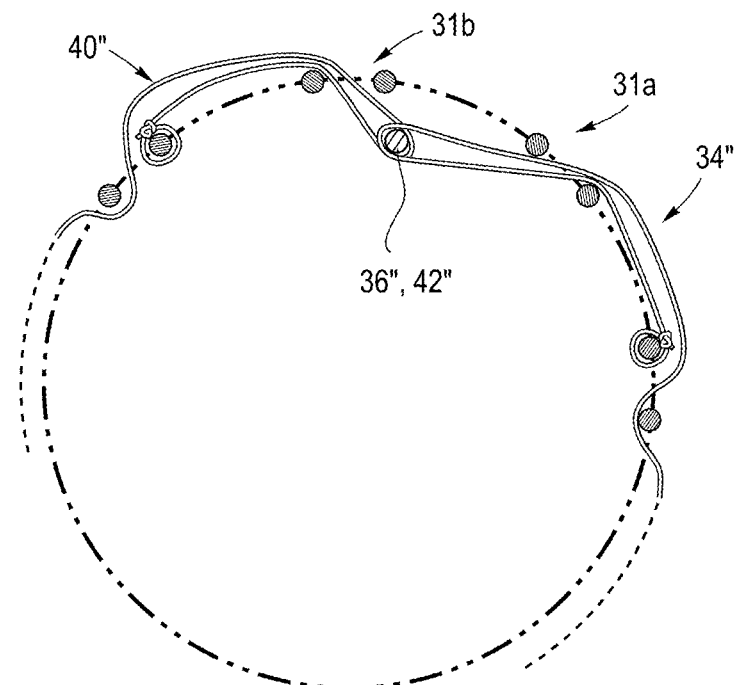

FIG. 18 is a view of a system according to an embodiment which is the same as the embodiment of FIG. 1, including details of manufacture and use, except as discussed below. FIG. 18 is a cross-section through the stent graft system in the region of the strand section and looking distally, with the stent graft in the constricted configuration.

As shown in FIG. 18, in this system there are first 31a and second 31b holding apices in the second circumferential region. In this embodiment these are adjacent distal apices of the sealing stent, but in other embodiments they could be separated by further intermediate distal apices. The first tail 34" passes through the wall of the graft body 14 between the struts of the first holding apex 31a and the second tail 40" passes through the wall of the graft body 14 between the struts of the second holding apex 31b. The first and second loops 36", 42" are retained by the trigger wire as discussed above. In this embodiment, therefore, the first and second tails together span three distal interstices in the constricted configuration of the stent graft.

It is possible in some embodiments for the first and second loops to be retained by different trigger wires. However, it is preferable for them to be retained by the same trigger wire so that the sealing stent 20 expands symmetrically. Although in the above embodiments the strand section is configured to constrict the sealing stent, in other embodiments it can be configured to constrict other stents along the graft body.

As discussed above, the first and/or second tails extend around part of the exterior of the graft body in the constricted configuration, however, it is not excluded that they can extend against an interior surface of the graft body in some embodiments for example such that a majority of each of the first and/or second tails extends against an interior surface of the graft body.

Although, the first and second tails are shown extending from the first and second ends of the strand section, in other embodiments the first and second tails can extend from other points of attachment of the strand section to the stent graft, such as points where the strand section loops around a strut at an apex of the sealing stent. This can be done for example by pulling a bight of the strand section circumferentially past these points. However, such embodiments are less preferable as they result in the strand section being laid triple in the regions of the tails.

Although, as shown the strand section is disposed at the distal end of the stent to be constricted, in other embodiments it can be disposed at any longitudinal location of the stent to be constricted, or even longitudinally offset from the stent to be constricted. Further, although all of the strand section from the first end to the second end is disposed in the first circumferential region in the expanded configuration, this is not necessary in every embodiment. In some embodiments it is possible that the first and/or second portion extends slightly outside the first circumferential region in the expanded configuration. However, this is not preferred as having all of the strand section in the first circumferential region can minimise the profile of the device. Preferably, at least a majority of the strand section, including a majority of the first portion and/or second portion, is disposed in the first circumferential region of the stent graft in the expanded configuration.

Although the tubular medical device to be constricted is disclosed as a stent graft including a stent, this is not essential in every embodiment. The diameter reducing arrangement may be used to constrain any tubular medical device from one diameter to a smaller diameter.

All optional and preferred features and modifications of the described embodiments and dependent claims are usable in all aspects of the invention taught herein. Furthermore, the individual features of the dependent claims, as well as all optional and preferred features and modifications of the described embodiments are combinable and interchangeable with one another.

The disclosures in the abstract accompanying this application are incorporated herein by reference. Although the embodiments are described separately, the features of an embodiment may be included with other embodiments.

The invention claimed is:

1. A medical device system, comprising:
   a tubular medical device comprising a tubular graft body having a proximal end and a distal end;
   a diameter reducing arrangement configured for constricting a diameter of the medical device, the diameter reducing arrangement including a strand section having first and second ends and being secured to the medical device at the first end and at the second end, the second end being a first circumferential distance from the first end by way of a path along the strand section;
   wherein, in a constricted configuration of the medical device, a first portion of the strand section extends back on itself to form a first double-stranded tail leading to a first loop, the first double-stranded tail extending circumferentially against the graft body to constrict the medical device by the strand section restricting the first circumferential distance between the first and second ends of the strand section.

2. The medical device system of claim 1, wherein the first and second ends of the strand section are immovably secured to the medical device.

3. The medical device system of claim 1, wherein in the constricted configuration, the first tail extends double-stranded circumferentially along a surface of the tubular graft body, wherein the surface is an external surface, an internal surface or both of the external and internal surfaces.

4. The medical device system of claim 1, wherein the first portion of the strand section passes and is laid double circumferentially beyond the first end to form the first tail and first loop.

5. The medical device system of claim 1, wherein the first circumferential distance traverses and defines a first circumferential region of the medical device, and wherein, in an expanded configuration of the medical device, at least a majority of the strand section is disposed in the first circumferential region of the medical device.

6. The medical device system of claim 1, wherein the first circumferential distance traverses and defines a first circumferential region of the medical device, wherein in an expanded configuration of the medical device at least a majority of the first portion is disposed in the first circumferential region of the medical device.

7. The medical device system of claim 1, wherein the first circumferential distance traverses and defines a first circumferential region of the medical device, and wherein, in the constricted configuration, the first portion extends outside the first circumferential region.

8. The medical device system of claim 1, wherein the first loop is retained by a release mechanism to hold the medical device in the constricted configuration.

9. The medical device system of claim 1, wherein the medical device is a stent graft including at least one stent.

10. The medical device system of claim 9, wherein the first and second ends of the strand section define first and second mutually exclusive circumferential regions of the stent graft with the first circumferential region of the stent graft extending from the first end to the second end of the strand section;

wherein the stent comprises a first end and a second end and a plurality of first apices at the first end of the stent; and wherein the strand section is disposed at and configured to constrict the first end of the stent.

11. The medical device system of claim 1, wherein the first and second ends of the strand section define a first circumferential region of the medical device from the first end to the second end of the strand section; and wherein, in an expanded configuration of the medical device, the first circumferential region extends around at least ⅟₇ of the circumference of the medical device.

12. The medical device system of claim 1, wherein the first tail passes through a wall of the tubular graft body and the first loop is retained by a release mechanism internally to the tubular graft body.

13. A diameter reduction system for a medical device comprising:

a tubular graft body having a proximal end and a distal end;

a stent disposed about the tubular graft body adjacent the proximal end of the tubular graft body and at least partially overlapping the tubular graft body;

a diameter reducing arrangement configured for constricting a diameter of the stent, the diameter reducing arrangement including a strand section having first and second ends, wherein the first end is attached to the stent at a first point on the stent and the second end is attached to the stent at a second point circumferentially spaced from the first stent to define a first circumferential distance from the first end by way of a path along the strand section to the second end;

wherein, in an expanded configuration, the first circumferential distance traverses and defines a first circumferential region of the tubular graft body in which a majority of the strand section is disposed;

wherein, in a constricted configuration of the medical device, a first portion of the strand section extends back on itself to form a first double-stranded tail leading to a first loop and a second portion of the strand section extends back on itself to form a second double-stranded tail leading to a second loop; and wherein, in the constricted configuration, the first double-stranded tail and the second double-stranded tail extend circumferentially about a surface of the graft body in opposite directions to constrict the stent to restrict the first circumferential distance between the first and second ends of the strand section.

14. The diameter reduction system of claim 13, wherein the first and second loops engage a releasable wire.

15. The diameter reduction system of claim 13, wherein in the constriction configuration the strand section entirely encircles the tubular graft and in the expanded configuration only partially encircles the graft.

16. The diameter reduction system of claim 13, wherein the strand section is woven in and out of the tubular graft.

17. The diameter reduction system of claim 13, wherein the first circumferential distance traverse and defines a first circumferential region of the medical device, and wherein, in the expanded configuration, the stent has a first distal apex within the first circumferential region, a second distal apex within the first circumferential, and a third distal apex disposed between the first and second distal apices and outside of the first circumferential region, and wherein the first end is secured to the first distal apex, the second end is secured to the second distal apex.

18. The diameter reduction system of claim 17, wherein the first end is permanently and immovably knotted to first apex and the second end is permanently and immovably knotted to the second apex.

19. A diameter reduction system for a medical device comprising;

a tubular graft body;

at least one stent disposed about the tubular graft body;

an expanded configuration;

a constricted configuration;

a diameter reduction strand disposed circumferentially about the tubular body; wherein the diameter reduction strand has a first terminal end immovably attached to the tubular body at one point on the tubular body and a second terminal end immovably attached to a point on the tubular body circumferentially spaced from the first point to define a length of the diameter reducing strand between the first and second point;

wherein, in the constricted configuration, a first portion of the diameter reduction strand at the first end extends back on itself to form a first double-stranded tail leading to a first loop, the diameter reduction strand is disposed fully circumferentially about the tubular body, and a releasable wire engages the first loop; and wherein, in the expanded configuration, the diameter reducing strand is disposed only partially circumferentially about the body, and upon release of the releasable wire, the first loop is released from its looped configuration.

20. The diameter reduction system of claim 19, wherein, in the constricted configuration a second portion of the diameter reduction strand at the second end extends back on itself to form a second double-stranded tail leading to a second loop engaged with the releasable wire, and wherein upon release of the releasable wire, the second loop is released from its looped configuration.

21. The medical device system of claim 9, wherein the at least one stent is attached at the proximal end of the tubular graft body.

22. The medical device system of claim 10, wherein in an expanded configuration of the stent graft the second circumferential region includes at least part of a first apex.

\* \* \* \* \*